United States Patent
Roach et al.

(10) Patent No.: US 9,459,369 B2
(45) Date of Patent: Oct. 4, 2016

(54) INDUCTIVE SENSOR WITH DEMODULATOR

(71) Applicant: Blue Line Engineering Co., Colorado Springs, CO (US)

(72) Inventors: Steven D. Roach, Colorado Springs, CO (US); Gregory H. Ames, Colorado Springs, CO (US); Philip N. Zercher, Colorado Springs, CO (US)

(73) Assignee: Blue Line Engineering Company, Colorado Springs, CO (US)

( * ) Notice: Subject to any disclaimer, the term of this patent is extended or adjusted under 35 U.S.C. 154(b) by 593 days.

(21) Appl. No.: 14/046,083

(22) Filed: Oct. 4, 2013

(65) Prior Publication Data
US 2014/0253107 A1    Sep. 11, 2014

(51) Int. Cl.
*G01V 3/10* (2006.01)
*G01P 3/49* (2006.01)
*G01D 5/22* (2006.01)

(52) U.S. Cl.
CPC ............. *G01V 3/10* (2013.01); *G01D 5/2275* (2013.01); *G01P 3/49* (2013.01)

(58) Field of Classification Search
CPC ......... G01V 3/10–3/108; G01D 5/20–5/2291; G01P 3/49–3/54

USPC .................................................. 324/207.12
See application file for complete search history.

(56) References Cited

FOREIGN PATENT DOCUMENTS

| EP | 1679492 A1 | 7/2006 |
|----|------------|--------|
| WO | 2012110756 A1 | 8/2012 |

OTHER PUBLICATIONS

Nabavi, Mohammed Reza , et al.; "Stability Considerations in a New Interface Circuit for Inductive Position Sensors"; Electronic Instrumentation Laboratory, Delft University of Technology, Delft, the Netherlands; IEEE Electronics, Circuits, and Systems, Piscataway, NJ, USA, Dec. 13, 2009, pp. 932-935.

Nabavi, Mohammed Reza, et al.; "Eddy-Current Sensor Interface for Advanced Industrial Applications"; IEEE Transactions on Industrial Electronics, IEEE Service Center, Piscataway, NJ, USA, Sep. 1, 2011, pp. 4414-4423.

*Primary Examiner* — Vincent Q Nguyen
*Assistant Examiner* — Rahul Maini
(74) *Attorney, Agent, or Firm* — Martensen IP (57) ABSTRACT

A transconductor converts voltage on an inductive sensor to a proportional current using two "coupling" capacitors. Responsive to movement of an electrically conductive target from the null position a resonant current is formed between the two sensor coils. A single differential transistor pair switched by periodic drive signals commutes the net alternating current at the single input to direct current.

14 Claims, 10 Drawing Sheets

PRIOR ART DEMODULATOR

INDUCTIVE SENSOR WITH DEMODULATOR

STATEMENT REGARDING FEDERAL SPONSORED RESEARCH OR DEVELOPMENT

This invention was made with U.S. Government support under HQ0147-12-C-7810 awarded by the U.S. Missile Defense Agency. The U.S. Government has certain rights in the invention.

RELATED APPLICATION

The present application relates to and claims the benefit of priority to U.S. Provisional Patent Application No. 61/710,565 filed 5 Oct., 2012 which is hereby incorporated by reference in its entirety for all purposes as if fully set forth herein.

BACKGROUND OF THE INVENTION

1. Field of the Invention

Embodiments of the present invention relate, in general, to inductive sensors and more particularly to a low noise inductive sensor with coupled capacitors.

2. Relevant Background

An inductive sensor is comprised of an induction loop that, when electric current passes through it, generates a magnetic field. In electromagnetism and electronics, inductance is the property of a conductor by which a change in current in the conductor "induces" (creates) a voltage (electromotive force) in both the conductor itself (self-inductance) and any nearby conductors (mutual inductance). To add inductance to a circuit, electronic components called inductors are used, typically consisting of coils of wire to concentrate the magnetic field and so that the magnetic field is linked into the circuit. The inductance of such a loop changes according to the material inside the magnetic field and since metals are much more effective inductors (conductors) than other materials the presence of metal in the magnetic field changes the current flowing through the loop. This change can be detected by sensing circuitry.

Inductive sensors are used in science, engineering, industry and medicine to measure a wide variety of physical phenomena. For example, metal detectors at airports are essentially inductive sensors as are control systems for traffic lights. Consider the pavement sensors near an intersection. These sensors can include one or more wire loops positioned within the pavement such that when a large metal mass approaches the loop, such as an automobile, the current within the loop changes. The inductive sensor described broadly above is referred to as an eddy current (EC) sensor. Eddy currents are created when a conductor experiences changes in the magnetic field. If either the conductor is moving through a steady magnetic field, or the magnetic field is changing around a stationary conductor, eddy currents will occur in the conductor. Therefore, eddy currents will be generated wherever a conducting object experiences a change in the intensity or direction of the magnetic field at any point within it, and not just at the boundaries. Eddy current sensors induce and detect eddy currents in electrically conductive bodies such as metals, liquids, industrial coatings and biological tissue. Such sensors can also measure material characteristics such as corrosion, cracking, wear and damage and are extensively used in the field of non-destructive testing (NDT).

Beyond basic metal detectors, EC sensors are particularly well suited to measuring the position or displacement of a metallic object because they are highly sensitive to position and motion while being highly insensitive to environmental factors such as dirt, water, temperature and radiation. EC sensors are often used in precision motion control systems such as the fine steering mirrors in satellite optics. In these systems the EC sensor provides motion feedback on the tip and tilt of a servo-controlled mirror used, for example, to image objects on the ground or to point a laser beam at another satellite. However, noise, or unwanted random signals, in the EC sensors causes the fine steering mirror to move unpredictably, generating "optical jitter" and degrading image quality or pointing accuracy. Therefore, there is a continued need for EC sensors with lower noise and higher accuracy.

Figure 1:
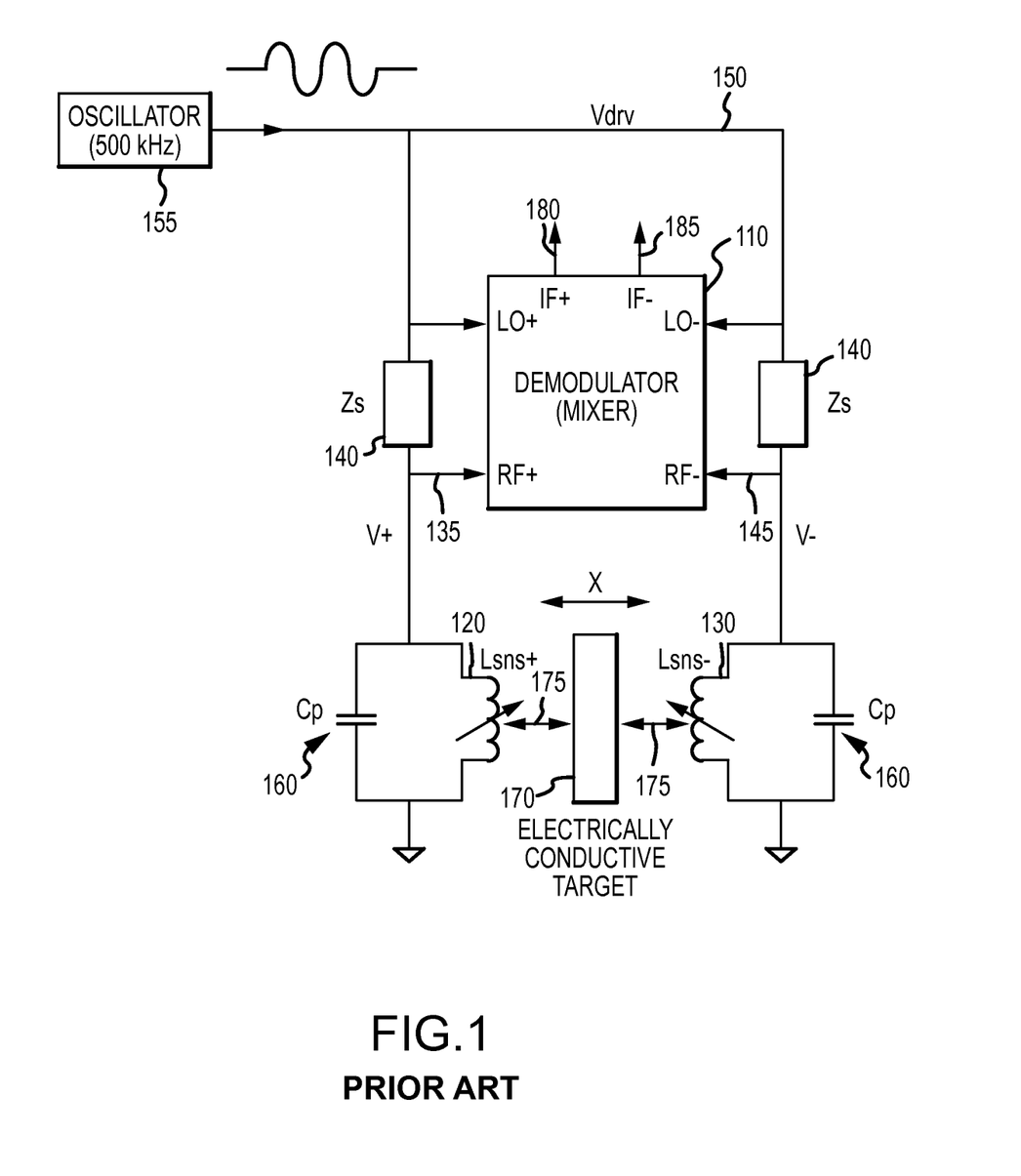
FIG. 1 shows a block diagram of a differential sensor circuit as would be known to one of reasonable skill in the relevant art.

FIG. 1 shows the arrangement of a differential eddy current sensor as would be known in the prior art. In this prior art example, the driver/demodulator block 110 drives the sensor coils, Lsns+ 120, and Lsns− 130, through the series elements Zs 140, which can be a resistor, inductor or capacitor or combination thereof. The drive signal 150, Vdrv, drives the two sensors 120, 130 with a sine wave, square wave, or similar periodic waveform generated from an oscillator 155 that is typically 500 kHz. Parallel capacitors Cp 160 resonate with the inductance of the sensors, improving linearity, temperature coefficient, and noise while reducing power consumption. The sensors are energized with an AC current at the drive signal frequency, and the magnetic field generated by the current induces eddy currents in the conductive target 170. The eddy currents generate an opposing magnetic field that can be sensed as an impedance change at the terminals of the sensor coil. The impedance change depends on the "lift-off," 175 or distance from the sensor coil to the target, so the voltages at RF+ 135 and RF− 145 vary in amplitude and phase in response to target movement. The demodulator 110 converts the AC signal at RF+ 135 and RF− 145 to DC (or baseband) at IF=V(IF+180−IF−185). IF 180, 185 may be filtered, offset, scaled or digitized in a downstream signal processing stage (not shown.)

When a target 170 is positioned precisely equidistant from the sensors 120, 130 (the null point), the sensor voltages RF+ 135 and RF− 145 are balanced with equal amplitude and equal phase. As the target 170 moves, it changes the inductance of the two sensor coils 120, 130 in a complementary way, unbalancing the voltages RF+ 135 and RF− 145. The demodulator 110 typically processes the difference (RF+−RF−) to produce a proportional DC signal at IF.

Figure 2:
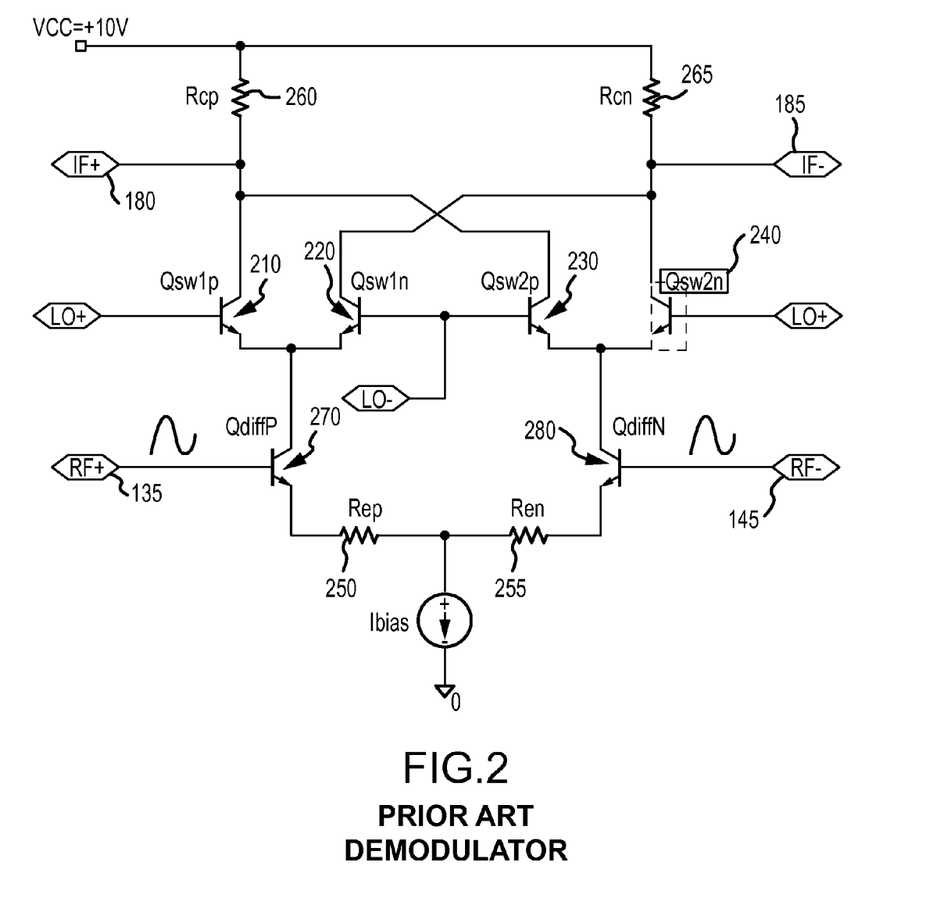
FIG. 2 shows a demodulator or mixer circuit as would be known to one or reasonable skill in the relevant art.

FIG. 2 shows a prior art demodulator circuit, which is also known as a standard Gilbert mixer. The demodulator circuit of FIG. 2 receives the voltages on the sensors at RF+135 and RF−145. The transistors QdiffP 270 and QdiffN 280 form a differential transconductor, converting the voltage difference (RF+−RF−) to a sinusoidal current which is fed into the switching quad comprised of Qsw1p, 210 Qsw1n, 220 Qsw2p, 230 and Qsw2n 240. These transistors are switched by the switch drive signals LO+ and LO− at the same frequency as the sensor drive signals, typically 500 kHz. The switching mixes the 500 kHz sensor signal (RF+−RF−) 135, 145 down to DC at IF+ 180 and IF− 185. Low pass filters, not shown, remove the 500 kHz signal and its harmonics producing IF=V(IF+−IF−).

The prior art demodulator shown in FIG. 2 has several shortcomings when used in an eddy current sensor system such as that shown in FIG. 1. For example, the transistors in the transconductor generate a significant amount of noise through their base resistance, base shot noise and collector shot noise. Moreover the transconductor has a limited common mode voltage range such that the circuit must be biased with high enough voltage to accommodate the full voltage swing on the sensors that appears largely in-phase at RF+ and RF−. This causes an increase in the minimum power supply voltage and therefore an increase in power dissipation.

The transconductor also adds an additional level of transistors to the switch transistors, requiring an increase in power supply voltage and power consumption, and the differential pair must be degenerated with the emitter resistors Rep 250 and Ren 255 to maintain adequate linearity and to control the temperature stability. Rep 250 and Ren 255 generate significant noise and can cause further voltage drops that require an increase in supply voltage and power consumption. While Rep 250 and Ren 255 could be replaced with inductors, inductors are usually physically larger and less temperature stable than resistors. Because Rep 250 and Ren 255 have relatively low impedance the transconductor must be biased with relatively high current to maintain linearity and temperature stability, further increasing noise and power dissipation.

Finally the finite current gain of the differential pair, QdiffP 270 and QdiffN 280, causes a loss of signal that is dependent on temperature and radiation exposure, degrading accuracy and stability, particularly in high radiation environments such as space. As can be seen above, there is a continued need for EC sensors with lower noise and higher accuracy. These and other deficiencies of the prior art are addressed by one or more embodiments of the present invention.

SUMMARY OF THE INVENTION

Disclosed hereafter by way of example is a current commutating demodulator (or "mixer") circuit for use in Radio Frequency (RF) communications and inductive sensors. Also disclosed are embodiments of an inductive sensor circuit. Embodiments of the circuit present a unique topology of a differential inductive sensor, replacing the transconductor found in prior art mixers and demodulators. A transconductor is a building block employed in many analog and mixed-signal circuit applications, such as continuous-time filters, delta-sigma modulators, variable gain-amplifiers or data converters that perform voltage-to-current conversion. In one embodiment of the present invention a transconductor converts voltage on the inductive sensor to a proportional current using two "coupling" capacitors. The configuration of the present invention converts the voltage-to-current circuit from a voltage-mode of the prior art to a current-mode, removing a number of design restrictions and performance limitations.

By converting the critical voltage-to-current circuit to a current mode, the noise, non-linearity and temperature sensitivity of the transconductor are nearly eliminated because the coupling capacitors are essentially noiseless, highly linear, and nearly temperature independent. Moreover the coupling capacitors allow the sensors to be driven with arbitrarily large AC signals, reducing noise without compromising linearity or requiring impractically high power supply voltages.

The coupling capacitors can also be freely scaled to maximize the baseband signal amplitude, minimizing the required post-amplification and further reducing noise and the new circuit can eliminate at least one source of radiation-induced drift by replacing the transconductor. Finally the new circuit is more power efficient than typical RF mixers because it needs less bias current to remain linear and temperature stable.

According to one embodiment of the present invention an inductive sensor circuit includes a demodulator, a first and second sensor coil and an electrically conductive target. The demodulator includes a single input and is operable to convert a net alternating current (AC) signal into a direct current (DC) signal. The first sensor coil is associated with a two capacitors wherein one capacitor is in parallel with the first sensor coil and the second capacitor is interposed in series between the single input of the demodulator and the first sensor coil. The second sensor coil is also associated with two capacitors, one in parallel with the second sensor coil and the other interposed in series between the single input of the demodulator and the second sensor coil. Both sensor coils are driven by drive signals that are 180° out of phase. Lastly an electrically conductive target is interposed between the first and second sensor coils such that when the target moves from a central, null, position the inductance on the sensor coils changes resulting in a net current at the single input of the demodulator.

Another feature of the demodulator of the present invention is that it includes a single differential transistor pair that is switched by drive signals that commute the net alternating current at the single input to direct current.

According to another embodiment of the present invention an inductive sensor circuit comprises a demodulator having a single input and an electrically conductive target interposed between a first and second sensor coil wherein the first sensor coil and the second sensor coil are coupled to the demodulator at the single input and wherein movement of the electrically conductive target from a null position generates a net alternating current at the single input.

The features and advantages described in this disclosure and in the following detailed description are not all-inclusive. Many additional features and advantages will be apparent to one of ordinary skill in the relevant art in view of the drawings, specification, and claims hereof. Moreover, it should be noted that the language used in the specification has been principally selected for readability and instructional purposes and may not have been selected to delineate or circumscribe the inventive subject matter; reference to the claims is necessary to determine such inventive subject matter.

BRIEF DESCRIPTION OF THE DRAWINGS

The aforementioned and other features and objects of the present invention and the manner of attaining them will become more apparent, and the invention itself will be best understood, by reference to the following description of one or more embodiments taken in conjunction with the accompanying drawings, wherein.

The Figures depict embodiments of the present invention for purposes of illustration only. One skilled in the art will readily recognize from the following discussion that alternative embodiments of the structures and methods illustrated herein may be employed without departing from the principles of the invention described herein.

DESCRIPTION OF THE INVENTION

Embodiments of the present invention are hereafter described in detail with reference to the accompanying Figures. Although the invention has been described and illustrated with a certain degree of particularity, it is understood that the present disclosure has been made only by way of example and that numerous changes in the combination and arrangement of parts can be resorted to by those skilled in the art without departing from the spirit and scope of the invention.

The following description with reference to the accompanying drawings is provided to assist in a comprehensive understanding of exemplary embodiments of the present invention as defined by the claims and their equivalents. It includes various specific details to assist in that understanding but these are to be regarded as merely exemplary. Like numbers refer to like elements throughout. In the figures, the sizes of certain lines, layers, components, elements or features may be exaggerated for clarity . Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The terminology used herein is for the purpose of describing particular embodiments only and is not intended to be limiting of the invention. As used herein, the singular forms "a", "an" and "the" are intended to include the plural forms as well, unless the context clearly indicates otherwise. Thus, for example, reference to "a component surface" includes reference to one or more of such surfaces.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be also understood that when an element is referred to as being "on", "attached" to, "connected" to, "coupled" with, "contacting", "mounted" etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The inductive sensor design of the present invention reduces noise and provides an improvement in accuracy over eddy current sensors and other inductive sensors. Since these sensors can be used to measure precise displacement and material properties in a wide variety of systems, the invention is potentially of use in a wide variety of applications, including precision position and displacement sensing in optics, robotics, semiconductor equipment, and industrial manufacturing applications.

Non-destructive inspection and testing of materials for cracks, corrosion, and other flaws and material characterization and quality control, such as measurement of electrical conductivity, magnetic permeability, thickness and the thickness of conductive and non-conductive coating are other applications for the present invention as are magnetic bearing servo systems.

The lower noise in the sensor leads to higher accuracy and higher sensitivity. Various embodiments of the present invention reduce noise, provide better linearity and increased temperature stability. The design also uses lower voltage and power as it is generally a more simplified circuit than those of the prior art.

Figure 3:
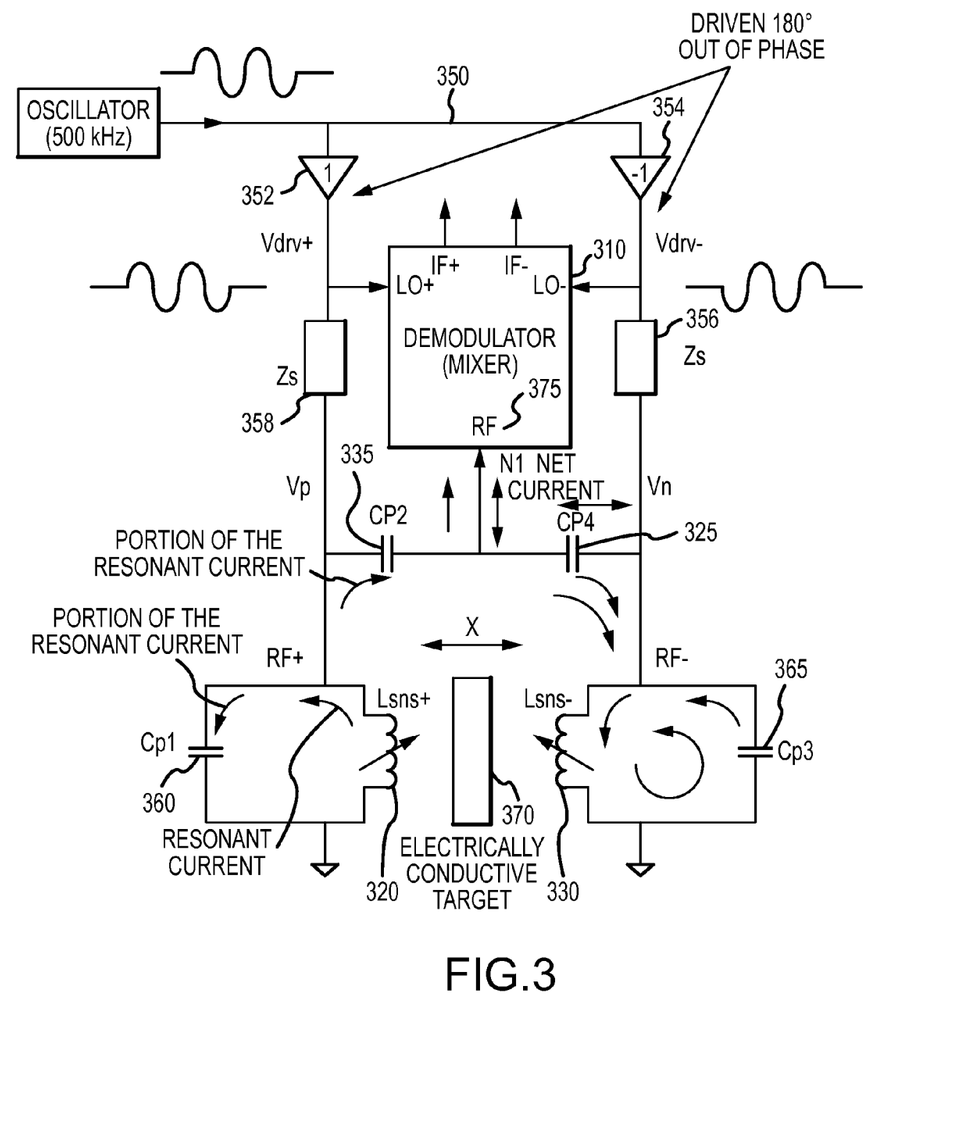
FIG. 3 is a circuit diagram of an improved inductive circuit with a coupled capacitor and two inductive sensors driven 180 degrees out of phase according to one embodiment of the present invention.

FIG. 3 shows a block diagram an improved inductor sensor circuit according to one embodiment of the present invention. A signal generated by an Oscillator 155 at typically 500 kHz provides a periodic signal 350 that is split into two drive signals Vdrv+ 352 and Vdrv− 354 that are 180° out of phase. These two signals, Vdrv+ 352 and Vdrv− drive a demodulator/mixer 375. The signal passes through a series of elements Zs which can be resistors, capacitors, inductors or any combination thereof to arrive at a signal Vp and Vn that drivers two inductive sensors Lsns+ 320 and Lsns− 330. As with the prior art the drive signal is periodic in nature however in this embodiment the drive signal is 180° out of phase. Each inductive sensor Lsns+ 320 and Lsns− 330 is associated with a capacitor Cp1 360 and Cp3 365, respectively, configured in parallel, that shunts a portion of the current from a resonant current produced by the sensor.

Interposed between the two inductive sensors Lsns+ 320, Lsns− 330 is an electrically conductive target 370. As the target moves from a middle (null) position the inductance in each of the two sensors is changed resulting in a resonant current or resonant frequency RF. For illustration purposes two counterclockwise currents are shown in sensor Lsns+ 320 and Lsns− 330. One skilled in the art will appreciate that no current exists when then target 370 is at a null position. Also, a clockwise current exists in both sensors Lsns+ 320. Lsns− 330 when the target 370 moves in the opposite direction.

As shown the demodulator 310 includes a single input or low impedance node N1 375. The node N1 375 is maintained essentially at AC ground. The single input N1 375 is coupled to each inductive sensor Lsns+ 320, Lsns− 330 through an additional capacitor Cp2 335, Cp4 325, respectively. According to one embodiment of the present invention capacitors Cp2 335, Cp4 325 possesses the same capacitance.

When the target is at the null point, RF+ and RF− are equal in amplitude and 180° out of phase, so the AC voltage on node N1 375 is zero and no net AC current flows into the demodulator 310 at node N1 375. When the target is displaced from the null point the sensor inductances are unequal, RF+ differs from RF− in amplitude and phase, and a net AC current flows into node N1 375.

Figure 4:
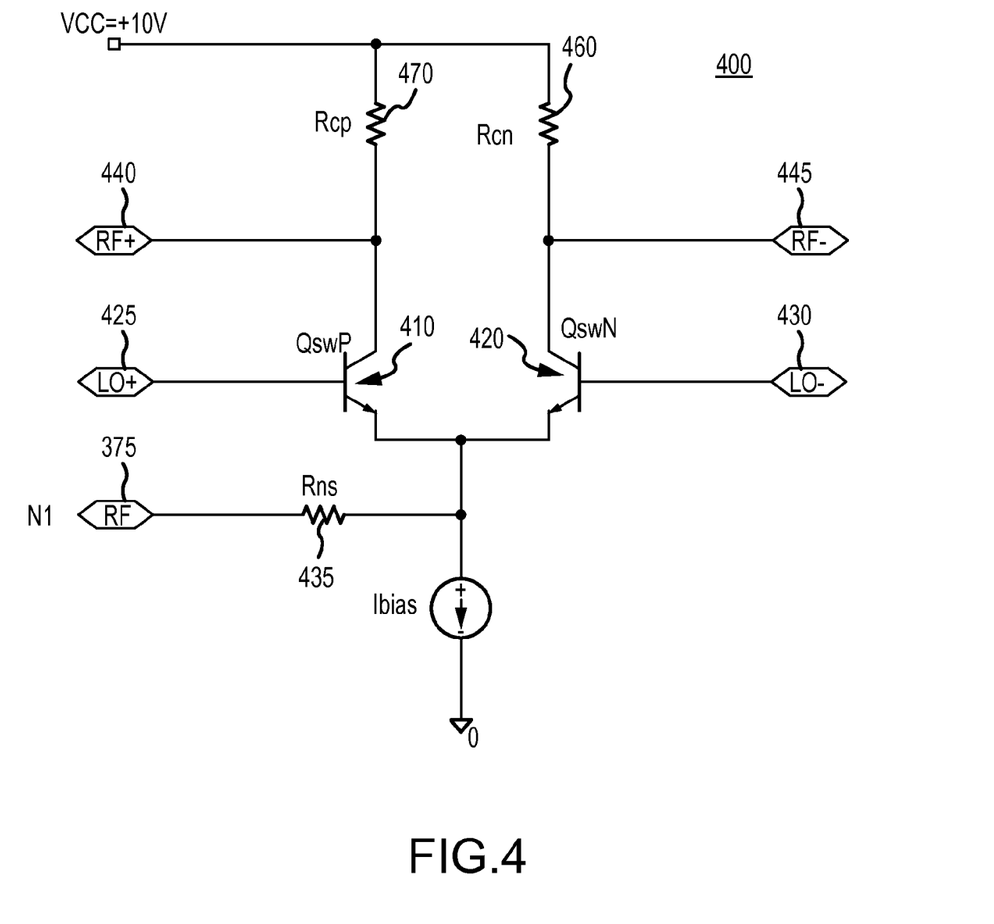
FIG. 4 is a demodulator circuit diagram for an improved inductive circuit according to one embodiment of the present invention.

FIG. 4 is a circuit diagram of a demodulator suitable for receiving a single AC input according to one embodiment. The demodulator 400 of the present invention includes a single differential NPN transistor pair, QswP 410 and QswN 420, that are switched by LO+ 425 and LO− 430 at the frequency of signal 350, which is typically 500 kHz. Net current from the sensors, RF, enters the low impedance emitters of the transistors, so N1 375 is maintained near AC ground. The transistors 410, 420 commutate this current, mixing the sensor frequency from 500 kHz down to DC at the IF+ 440 and IF− 445 outputs. Resistor Rns 435 isolates the sensors Lsns+ 320, Lsns− 330 and the capacitors Cp1 360, Cp3 365 and Cp2 335, Cp4 325 respectively, from the emitters of the transistors, reducing noise and improving the high frequency stability of the transistors. According to one embodiment of the present invention, capacitors Cp1 360 and Cp3 365 can possess the same capacitance. Also, one of reasonable skill in the art will recognize that resistor Rns 435 may be replaced with an arbitrary impedance 470, 460 such as an inductor for the same purpose.

The inductive sensor of FIG. 3 and demodulator of FIG. 4 provide significant advantages over the prior art. The noise, non-linearity, temperature sensitivity and radiation sensitivity of the prior art transconductor (illustrated by example in FIGS. 1 and 3) are nearly eliminated. The coupling capacitors, CP2 335 and CP4 325, substantially reduce noise to the point of being essentially noiseless, demonstrating highly linear characteristics, and are nearly immune to temperature drift and radiation degradation.

In contrast to the input of the prior art demodulator circuit (for example voltage input RF+ 135, RF− 145), embodiments of the current invention convert the input to a current input at node N1 375, so the demodulator 310, 400 is oblivious to the full voltage on the sensors. The capacitors, CP2 335 and CP4 325, are also highly linear further aiding to the improved characteristics of the circuit. These factors allow the sensors Lsns+ 320, Lsns− 330, to be driven with a relatively large signal 350 to minimize noise. These factors also permit a reduction in the power supply voltage, reducing total power consumption.

As illustrated in FIG. 3 the coupling capacitors Cp2 335, Cp4 325 are connected to a low impedance node N1 375, so they are essentially held at AC ground. Thus the capacitors experience very little additional series resistance, preserving and enhancing their high quality factor, reducing noise, and increasing sensitivity to target movement. These capacitors also see zero additional series resistance at the null point, as there is no net current that flows into N1 when the target is in its null position. Therefore there is zero degradation in quality factor at the null point, which is significant in mechanical servo systems such as magnetic bearing control and alignment of segmented mirrors in astronomical telescopes, aiming devices and the like. In those applications, and many others, the servo system drives and maintains the target position at the null point where accuracy and low noise is critical.

The new demodulator 400 illustrated in FIG. 4 taps a portion of the current circulating in the sensors at Lo+ 425 and Lo− 445. In practice the circulating current can be relatively large (e.g., tens of milliamps in a typical system). By changing the ratio of Cp1 360, Cp3 365 and Cp2 335, Cp4 325 any portion of the circulating current can be routed into the demodulator. Thus the demodulator can work with a large current-mode input signal rather than the relatively weak voltage mode signal in the prior art. The demodulator 400 can therefore develop higher gain (also known as conversion gain) than the circuits of the prior art. Such a higher gain minimizes or even eliminates the need for post amplification of the demodulator output, IF+ 440, IF− 445.

The effects of noise in the demodulator 400 and the downstream circuits (filter, amplifiers, ADC and the like) are therefore reduced.

Embodiments of the current circuit are also more power efficient than the circuits of the prior art because they need less bias current to remain linear and temperature stable. The impedance of the capacitors Cp2 335, Cp4 325 is, according to one embodiment of the present invention, higher than the impedance seen at the emitters of the transistors QswP 410 and QswN 420. In addition and according to another embodiment of the present invention, the impedance of capacitors Cp2 335, Cp4 325 is higher that the resistance Rep 250 and Ren 255 the prior art circuit shown in FIG. 2. The lower bias current reduces power but also reduces noise because it reduces transistor base and collector shot noise.

Figure 5:
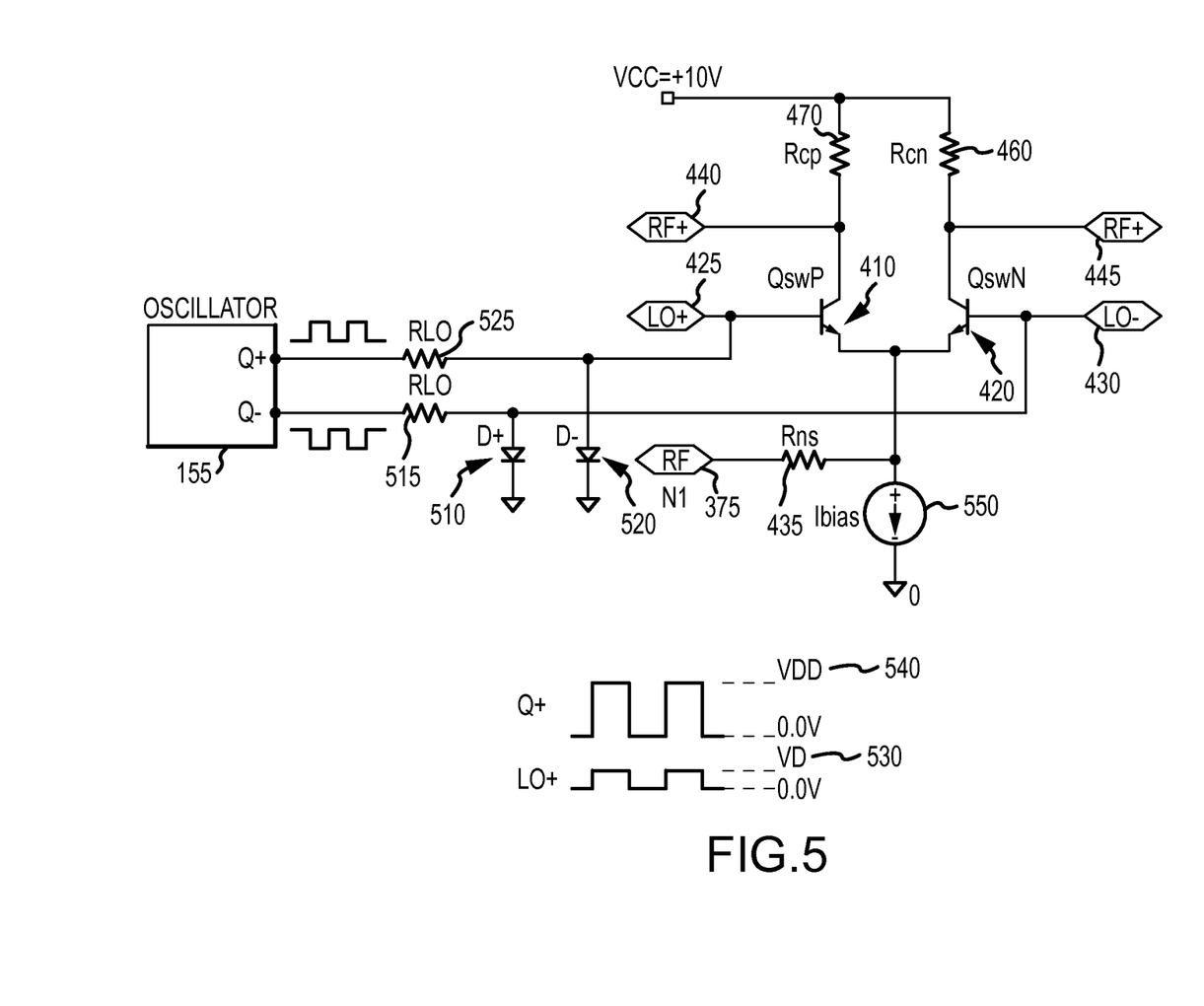
FIG. 5 is a circuit diagram of a local oscillatory driver according to one embodiment of the present invention.

FIG. 5 is a circuit diagram of a local oscillatory driver according to one embodiment of the present invention. The local oscillatory driver of FIG. 5 reduces the effects of variations in the emitter voltage of QswP 410 and QswN 420. Diodes D+ 510 and D− 520 clamp the LO+ 425 and LO− 430 signals to the voltage VD 530 above ground, where VD 530 is the forward biased diode voltage. The emitter voltage rises to VD 530−VBE, where VBE is the base-emitter voltage of the transistors. Even if the oscillator output voltages, Q+ and Q−, fluctuate or ring, the diodes D+ 510, D− 520 will attenuate the variation at the LO+ 425 and LO− 430 nodes.

The diodes D+ 510, D− 520 can, in one embodiment of the present invention, be made with diode connected NPN transistors that match QswP 410 and QswN 420. In that case the emitter voltage will be temperature and radiation compensated to a great degree, stabilizing the voltage on the bias current source Ibias 550. This in turn helps stabilize the bias current, particularly if Ibias 550 is made merely with a resistor.

Figure 6:
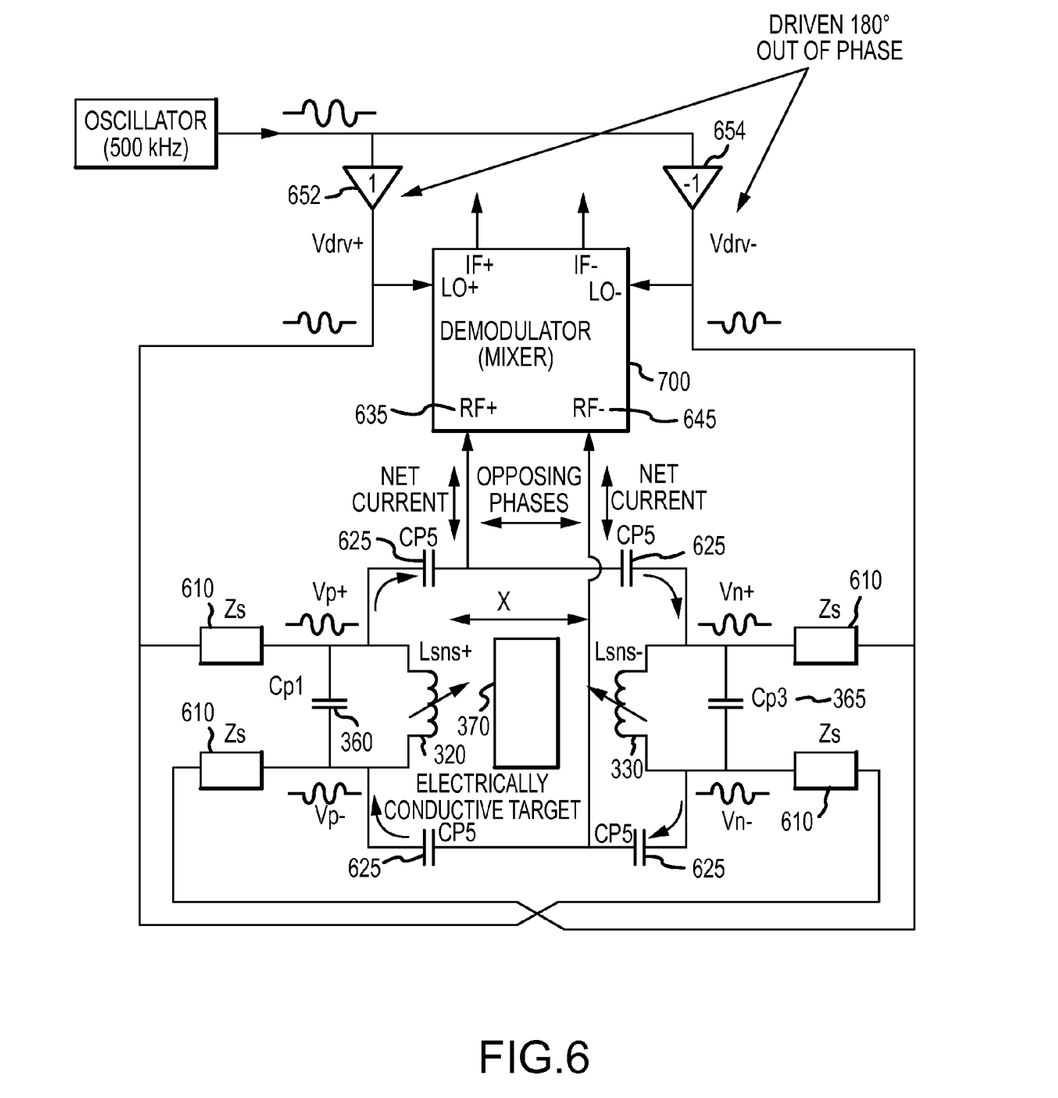
FIG. 6 is a high level block diagram of an improved inductive circuit according to one embodiment of the present invention that is driven differentially, 180 degrees out of phase, and combined with a differential sensor drive.

FIG. 6 is a high level block diagram of an improved inductive circuit according to one embodiment of the present invention that is driven differentially, 180 degrees out of phase, and combined with a differential sensor drive. In the embodiment of the present invention shown in FIG. 6, the two sensors, Lsns+ 320, Lsns− 330, are driven differentially and are 180 degrees out of phase.

Vdrv+ 652 and Vdrv−654 are periodic (sine wave or square wave) signals that are applied to both sensor terminals, Lsns+ 320, Lsns− 330, through the four series impedances Zs 610. Four capacitors Cp5 625 couple the sensor voltages into two low-impedance inputs RF+ 635 and RF− 645 to the demodulator. The voltages on the sensor terminals are labeled Vp+, Vp−, Vn+ and Vn−. At the null point, or the point at which the target 370 is equidistant from the two sensors Lsns+ 320, Lsns− 330, the two sensors have equal impedances and the circuit operates in a symmetrical mode. Vdrv+ 652 and Vdrv− 654 are 180° out of phase, so Vdrv+ 652=−Vdrv−654. By symmetry we see that Vp+=−Vp− and Vn+=−Vn−. Also by symmetry Vp+=−Vn+ and Vp−=−Vn− and there is no net current flowing into nodes RF+ 635 and RF− 645. As the target 370 moves away from the null point, the sensor impedances become unequal and net current flows into RF+ 635 and RF− 645. However, symmetry also reveals that the current into RF+ 635 is equal and opposite that in RF− 645. The demodulator 700 processes these currents, mixing them down to DC.

Figure 7:
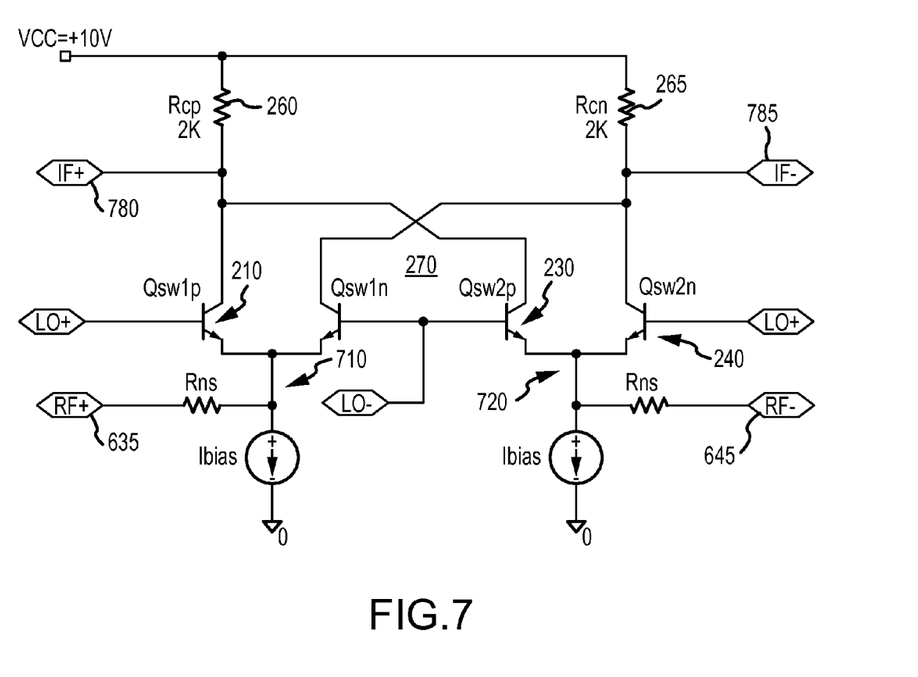
FIG. 7 is a demodulator for the differentially driven circuit of FIG. 6, according to one embodiment of the present invention.

A demodulator circuit 700, according to another embodiment of the present invention, for the differential driven system in FIG. 6 is shown in FIG. 7. This circuit differs from the double-balanced mixer shown in FIG. 2 in that the differencing function of the transconductor is performed by coupling capacitors, Cp5 625 (shown in FIG. 6). As can be seen in FIG. 7, and as compared to the demodulator of FIG. 2, the two switching pairs (Qsw1p 710/Qsw1n 770 and Qsw2p 730/Qsw2n 740) are coupled directly 710, 720 to the emitters RF+ 635 and RF− 645. LO+ and LO− are periodic (sine wave or square wave) signals that fully switch their current in these pairs. The signals from the sensors Lsns+ 320, Lsns− 330 in FIG. 6 are injected into the emitters 710, 720 of the switching pairs (Qsw1p 710/Qsw1n 770 and Qsw2p 730/Qsw2n 740) at the low-impedance nodes RF+635 and RF−645. The switching pairs commutate the current from the sensors, mixing the AC sensor signal down to DC at the nodes IF+ 780 and IF− 785.

According to one embodiment of the present invention, driving the sensors with complementary signals at Vdrv+ 652 and Vdrv− 654 doubles the voltages across the sensors Lsns+ 320, Lsns− 330. This increase in voltage decreases noise and increases immunity to radio-frequency interference (RFI). Moreover, the noise power contributed by the demodulator and downstream electronics is nominally halved. The balanced connections to both terminals of each sensor Lsns+ 320, Lsns− 330 helps reject RFI because RFI now appears as a common mode signal that can be rejected by the differential symmetry of the demodulator 700.

Compared to demodulator circuit shown in FIG. 4, which is a version of a single-balanced mixer, the double-balanced configuration of the demodulator depicted in FIG. 7 suppresses local oscillator (LO) feed through, making the demodulator output significantly easier to filter.

Figure 8:
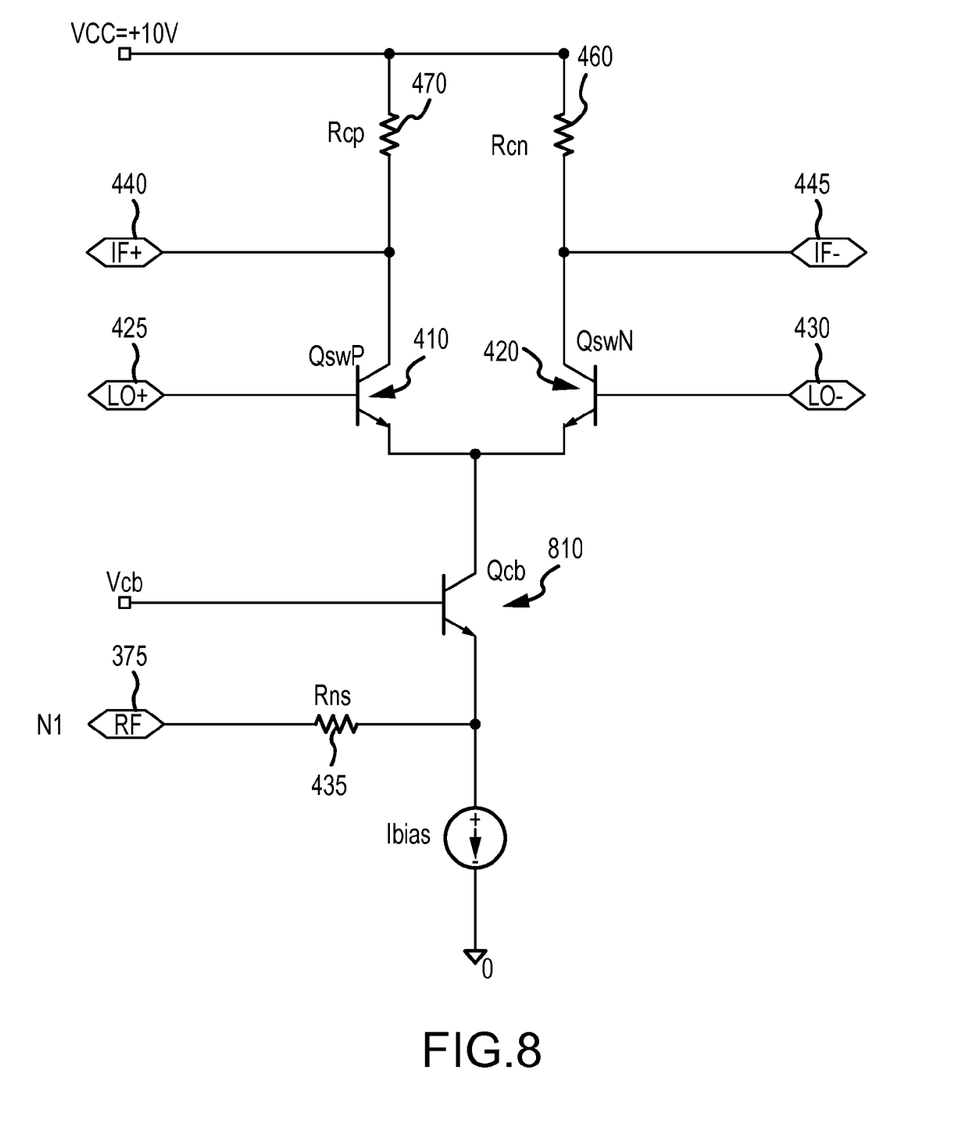
FIG. 8 is a demodulator circuit with a common base input stage according to one embodiment of the present invention.

FIG. 8 is a demodulator circuit with a common base input stage according to one embodiment of the present invention. As shown a common base transistor Qcb 810 is coupled to the emitter of the switching pair QswP 410, QswN 420.

Figure 9:
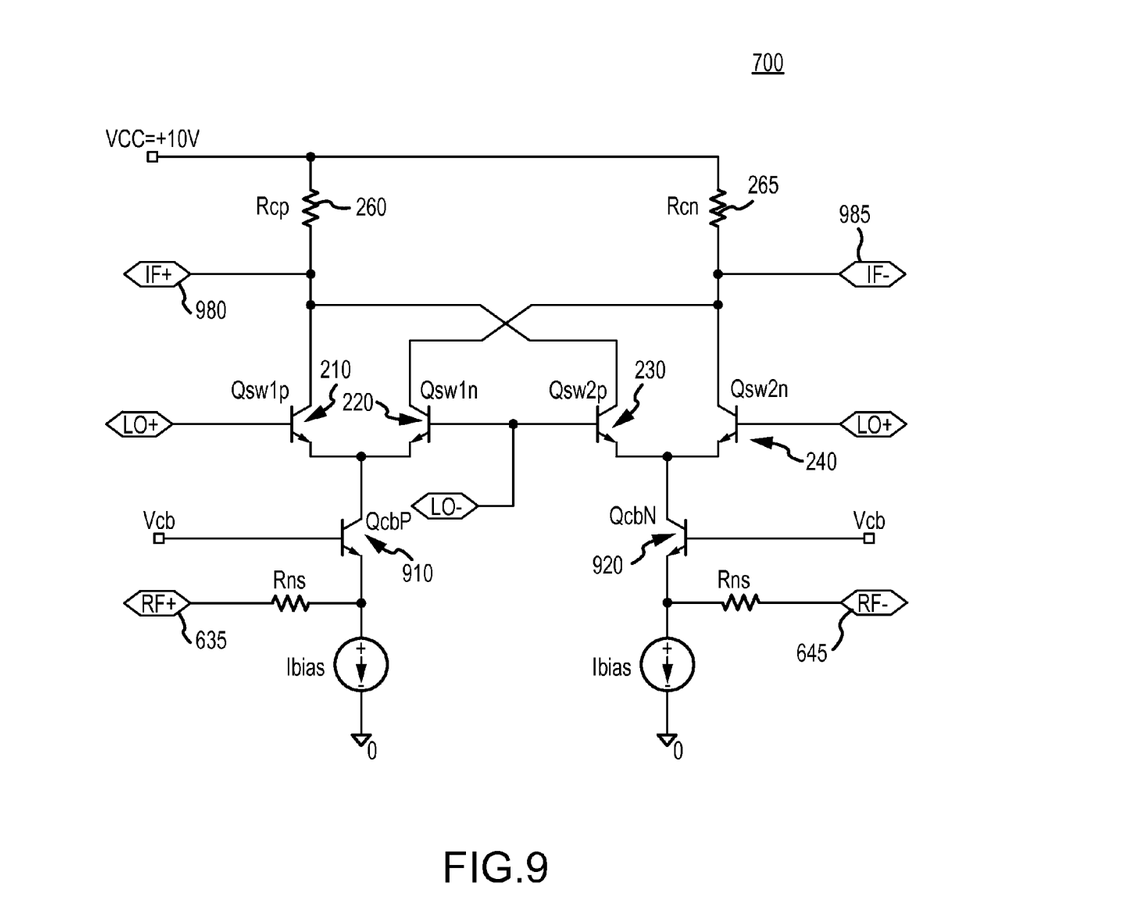
FIG. 9 is a demodulator for a differentially driven circuit with a common base input stage according to one embodiment of the present invention.

FIG. 9 shows a demodulator for a differentially driven circuit with a common base input stage according to one embodiment of the present invention. In the demodulator of FIG. 9 common base transistors QcbP 910 and QcbN 920 are coupled to the emitters of the switching pairs (Qsw1p 710/Qsw1n 770 and Qsw2p 730/Qsw2n 740).

Figure 10:
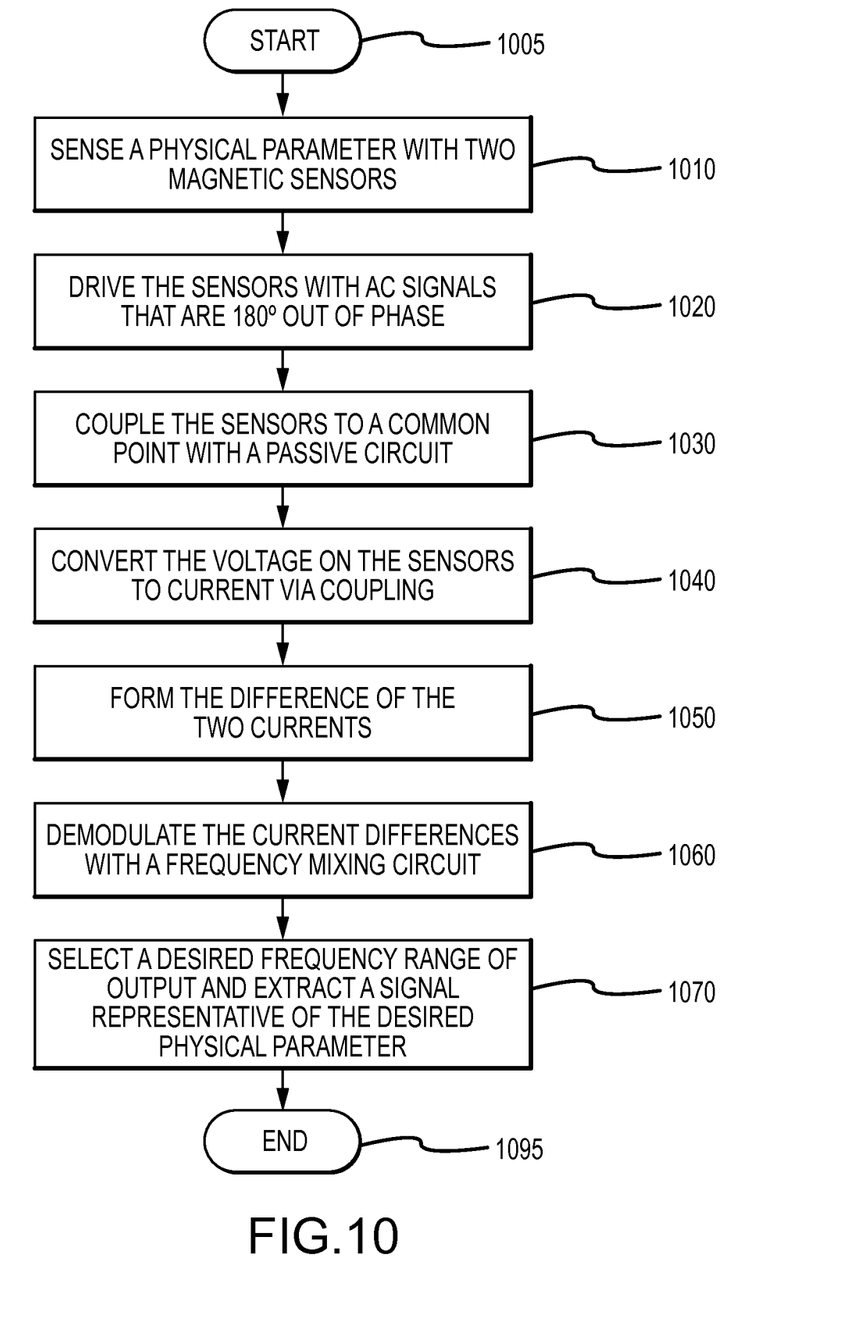
FIG. 10 is a flowchart of one method for demodulating a current difference with a frequency mixing circuit according to one embodiment of the present invention.

According to another embodiment of the present invention a demodulator or mixer circuit for use in Radio Frequency (RF) communications and inductive sensors uses current commuting to lower noise, increase reliability and provide improved versatility. FIG. 10 is a flowchart depicting one method embodiment of signal demodulation using current commutation. In the following description, it will be understood that each block of the flowchart illustrations, and combinations of blocks in the flowchart illustrations, can be implemented by on or more equivalent circuit designs. These circuits create a means for implementing the functions specified in the flowchart block or blocks shown in FIG. 10. Accordingly, blocks of the flowchart illustrations support combinations of means for performing the specified functions and combinations of steps for performing the specified functions. It will also be understood that each block of the flowchart illustrations, and combinations of blocks in the flowchart illustrations, can be implemented by special purpose hardware systems that perform the specified functions or steps, or combinations of special purpose hardware.

In this example the demodulation process begins 1005 with sensing 1010 a physical parameter with two magnetic sensors. As one of reasonable skill in the relevant art can appreciate the present invention can accept signals from a variety of type of sensors with equal effectiveness. The sensors are thereafter driven 1020 with an AC signal that is exactly 180 degrees out of phase. The sensors are moreover coupled to a common reference point 1030 with, in one embodiment, a passive circuit thereby automatically converting the two voltages to current 1040.

A difference between the two currents is determined 1050 that is then demodulated 1060 with a frequency mixing circuit. A desired frequency range can thereafter be selected 1070 with a filter or similar circuit configuration to extract a signal suitable for the physical parameter of interest.

While there have been described above the principles of the present invention in conjunction with an inductive sensor circuit, it is to be clearly understood that the foregoing description is made only by way of example and not as a limitation to the scope of the invention. Particularly, it is recognized that the teachings of the foregoing disclosure will suggest other modifications to those persons skilled in the relevant art. Such modifications may involve other features that are already known per se and which may be used instead of or in addition to features already described herein. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The Applicant hereby reserves the right to formulate new claims to such features and/or combinations of such features during the prosecution of the present application or of any further application derived therefrom.

We claim:

1. An inductive sensor circuit comprising:
    a demodulator having a single input (N1) operable to convert a net alternating current signal into a direct current signal;
    a first sensor coil (Lsns+) associated with a first capacitor (CP1) and a second capacitor (CP2) wherein the first capacitor (CP1) is in parallel with the first sensor coil (Lsns+) and the second capacitor (CP2) is interposed in series between the single input (N1) of the demodulator and the first sensor coil (Lsns+);
    a second sensor coil (Lsns−) associated with a third capacitor (CP3) and a fourth capacitor (CP4) wherein the third capacitor (CP3) is in parallel with the second sensor coil (Lsns−) and the fourth capacitor (CP4) is interposed in series between the single input (N1) of the demodulator and the second sensor coil (Lsns−) and wherein
    the first sensor coil (Lsns+) and the second sensor coil (Lsns−) are driven by respective drive signals (Vdrv+, Vdrv−) that are 180° out of phase; and
    an electrically conductive target interposed between the first sensor coil (Lsns+) and the second sensor coil (Lsns−) wherein movement of the electrically conductive target from a null position changes inductance on the first sensor coil (Lsns+) and inductance on the second sensor coil (Lsns−) generating the net alternating current at the single input (N1) at the demodulator.

2. The inductive sensor circuit of claim 1, wherein the demodulator includes a single differential transistor pair (QswP, QswN) that is switched by the drive signals (Vdrv+, Vdrv−) to commute the net alternating current signal at the single input (N1) to the direct current signal.

3. The inductive sensor circuit of claim 1, wherein the second capacitor (CP2) and the fourth capacitor (CP4) are connected to the input (N1) at the demodulator forming a current summing junction.

4. The inductive sensor circuit of claim 1, wherein each sensor coil of the first and second sensor coils each include a wire winding.

5. The inductive sensor circuit of claim 1, wherein the first capacitor (CP1) shunts a portion of resonant alternating current from the first sensor coil (Lsns+).

6. The inductive sensor circuit of claim 1, wherein the third capacitor (CP3) shunts a portion of resonant alternating current from the second sensor coil (Lsns−).

7. The inductive sensor circuit of claim 1, wherein capacitance of the first capacitor (CP1) and the third capacitor (CP3) are substantially equal.

8. The inductive sensor circuit of claim 1, wherein capacitance of the second capacitor (CP2) and the fourth capacitor (CP4) are substantially equal.

9. The inductive sensor circuit of claim 1, wherein the drive signals (Vdrv+, Vdrv−) are periodic waveforms.

10. The inductive sensor circuit of claim 1, wherein responsive to the electrically conductive target being in the null position, the second capacitor (CP2) and the fourth capacitor (CP4) experience substantially zero alternating current flow into the single input (N1) at the demodulator.

11. The inductive sensor circuit of claim 1, wherein responsive to movement of the electrically conductive target from the null position, a first resonant alternating current is formed between the first sensor coil (Lsns+) and the first capacitor (CP1) and a second resonant alternating current is formed between the second sensor coil (Lsns−) and the third capacitor (CP3).

12. The inductive sensor circuit of claim 11, wherein the demodulator taps a portion of the first resonant alternating current and the second resonant alternating current.

13. The inductive sensor circuit of claim 12, wherein the portion of the current tapped from the first resonant alternating current and the second resonant alternating current can be controlled by changing proportional values of the first capacitor (CP1) to the second capacitor (CP2) and/or proportional values of the third capacitor (CP3) to the fourth capacitor (CP4).

14. The inductive sensor circuit of claim 1 wherein the demodulator includes a single differential transistor pair (QswP, QswN) that is switched by the drive signals (Vdrv+, Vdrv−) that commute the net alternating current at the single input (N1) to the direct current signal.

* * * * *